United States Patent [19]

Pacheco et al.

[11] Patent Number: 5,338,878
[45] Date of Patent: Aug. 16, 1994

[54] ALKYL CARBONATE EXTRACTION PROCESS

[75] Inventors: Michael A. Pacheco, Naperville, Ill.; Franklin D. Darrington; Albert L. Hensley, Jr., both of Munster, Ind.

[73] Assignee: Amoco Corporation, Chicago, Ill.

[21] Appl. No.: 11,246

[22] Filed: Jan. 29, 1993

[51] Int. Cl.$^5$ ............................................. C07C 69/96
[52] U.S. Cl. .................................................. 558/277
[58] Field of Search ........................................ 558/277

[56] References Cited

U.S. PATENT DOCUMENTS 3,963,586  6/1976  Ginnasi et al. ............... 558/277 X
4,162,200  7/1979  Himmele et al. ............. 558/277 X Primary Examiner—Mary C. Lee
Assistant Examiner—Michael G. Ambrose
Attorney, Agent, or Firm—Thomas A. Yassen; Richard A. Kretchmer; Frank J. Sroka

[57] ABSTRACT

A process is provided for separating alkyl carbonate from a feedstock comprising at least one alkyl carbonate and at least one alkanol comprising extracting the alkyl carbonate from the feedstock in a liquid-liquid extraction step comprising a first extraction solvent comprising hydrocarbon selective for extracting alkyl carbonates relative to alkanol in an amount sufficient to extract a substantial portion of the alkyl carbonate from the feedstock and a second solvent comprising water in an amount sufficient to extract a substantial portion of the alkanol from the feedstock.

20 Claims, 1 Drawing Sheet

ALKYL CARBONATE EXTRACTION PROCESS

BACKGROUND OF THE INVENTION

This invention relies to a process for separating alkyl carbonate from feedstocks containing alkyl carbonate and alkanol. More particularly, this invention relates to a liquid-liquid extraction process for separating alkyl carbonate from feedstocks comprising alkyl carbonate, alkanol, and other components such as water, for uses such as the production of high oxygen-content gasoline blending components (Oxygenates).

Oxygenates have been part of the United States gasoline strategy since the late 1970s. With the Clean Air Act Amendments of 1990, the demand for oxygenates is expected to increase even further. For example, starting in the winter months of 1992, gasoline containing 2.7 weight percent oxygen will have to be provided to approximately 40 metropolitan areas that have failed to meet carbon monoxide pollution standards. It is expected that in the near future, between 30 and 60 percent of the United States gasoline pool may be required to contain oxygenates.

The most commonly used oxygenates today are methanol, ethanol, and methyl tertiary butyl ether (MTBE). Although methanol and ethanol have high blending octanes, problems with toxicity, water miscibility, high Reid Vapor Pressure (RVP), high nitrogen oxide emissions, lower fuel efficiency, and cost have dampened industry enthusiasm for these components. Partially as a result of the above, MTBE has become particularly attractive.

Homologues of MTBE such as ethyl tertiary butyl ether (ETBE) and methyl tertiary amyl ether (TAME) are also gaining industry acceptance. Moreover, commercial activity with respect to ETBE and TAME is expected to increase relative to MTBE, in view of the recent Environmental Protection Agency decision to reduce the RVP requirements for gasolines well below 9 psia, the blending RVP of MTBE.

Oxygenate production capacity, however, is limited by ether plant capacity and by feedstock availability. MTBE and ETBE both utilize isobutylene as a feedstock while TAME uses isoamylene as a feedstock. Isobutylene and isoamylene are generally supplied to an ether facility in a petroleum refinery from a fluid catalytic cracking unit (FCC), a fluidized or delayed coker, or from downstream paraffin isomerization and dehydrogenation facilities. The availability of hydrocarbons having 4 carbons is limited by constraints such as, but not limited to, crude properties, FCC catalyst properties, FCC operating conditions, coking conditions as well as other refinery operating constraints. The chemical mix of $C_4$ and $C_5$ paraffins, olefins, and aromatics as well as the particular mix of iso-olefins to normal olefins are similarly constrained.

Thus, there exists a great need in the petroleum industry for a low-cost method of increasing oxygenate production capacity that overcomes or avoids the obstacles described above.

The use of carbonates, and particularly the dialkyl carbonates in fuels has been the subject of several patents and patent applications.

European Patent Application Numbers 0 082 688 to Bretherick and 0 098 691 to Spencer disclose the use of dialkyl carbonate and dimethyl carbonate in fuels for use with spark ignition engines.

U.S. Pat. No. 4,380,455 to Smith discloses the use of dialkyl carbonates for preventing the phase separation of hydrous ethanol from liquid hydrocarbon fuel mixtures.

U.S. Pat. No. 4,891,049 to Dillon discloses the use of non-aromatic, metals-free carbonates for reducing particulate emissions from distillate-based fuels such as diesel fuel and jet fuel.

Carbonates can be produced using any of several methods known in the art, each method having attendant advantages and penalties. Such methods include the carbonylation of alcohols, alkylene carbonate alcoholysis, urea alcoholysis, inorganic methods, and phosgene alcoholysis.

One of the oldest methods for manufacturing carbonates employs phosgene. The phosgene is generally contacted with methanol to form methyl chloroformate in accordance with the following reaction:

$$CH_3OH + COCl_2 \rightarrow CH_3OCOCl + HCl$$

The methyl chloroformate reacts with an additional mole of methanol to form dimethyl carbonate as follows:

$$CH_3OCOCl + CH_3OH \rightarrow CH_3OCOOCH_3 + HCl$$

One associated penalty with the process described hereabove is that the process requires the use of toxic phosgene. Moreover, the method also leads to the co-production of other chloride-containing by-products such as alkyl chlorides, which can often be toxic themselves. Chlorine-containing by-products such as hydrogen chloride can also be particularly corrosive. Neutralization methods to balance the acidity of such chlorided components in order to mitigate such corrosive effects such as the addition of sodium hydroxide to drive the reaction by the production of sodium chloride and water, can be costly and can also compromise product quality.

Oxidative carbonylation is another method that has been used to produce carbonates. It is generally known that carbonates can be produced from alkanol and carbon monoxide in the presence of certain metal chlorides or metal alkoxy chlorides through an oxidation-reduction reaction. An example of such a reaction with methanol and carbon monoxide over a copper chloride catalyst is as follows:

Oxidation:

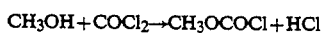
$$2CH_3OH + 1/2O_2 + 2CuCl \longrightarrow 2Cu(OCH_3)(Cl) + H_2O$$

Reduction:

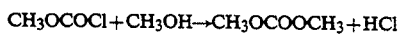
$$2Cu(OCH_3)(Cl) + CO \longrightarrow 2CuCl + CH_3O(CO)OCH_3$$

Overall:

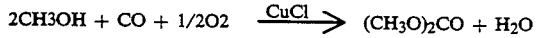
$$2CH_3OH + CO + 1/2O_2 \xrightarrow{CuCl} (CH_3O)_2CO + H_2O$$

U.S. Pat. No. 4,218,391 to Romano et al. discloses such a process for the production of carbonates comprising reacting an alkanol with oxygen and carbon monoxide in the presence of a catalyst consisting of a copper metal salt of the group of cuprous and cupric salts having a single inorganic anion.

U.S. Pat. No. 5,004,827 to Curnutt discloses a similar process for the production of carbonates comprising contacting an alkanol with carbon monoxide and oxygen in the presence of a heterogeneous catalyst comprising a metal halide such as cupric chloride with or without potassium chloride impregnated on an appropriate support such as activated carbon.

This reaction cannot generally be operated to high conversion because high concentrations of water in the reactor lead to low selectivity, i.e., high $CO_2$ yields. Additionally, excess water can lead to the formation of a variety of copper hydroxy chloride phases of the formula $Cu(Cl)_x(OH)_y \cdot nH_2O$. None of these phases are particularly effective for the production of carbonates.

For these, among other reasons, it is generally desirable that these reactions be conducted with a low conversion for each pass through the reactor with an effective strategy for feed/product separation and recycle of the unconverted feed.

Moreover, under typical oxidative carbonylation reaction conditions, the product stream generally comprises the alkyl carbonate, alkanol, and water, wherein the alkyl carbonate can form azeotropes with both the alkanol and water. For example, Table 1 illustrates the boiling point and composition of various binary azeotropes within a mixture comprising methanol, ethanol, dimethyl or diethyl carbonate, and water.

TABLE 1

| Boil. Pt. Temp. °C. | Pure Comp. | Azeotrope Comp.- Wt % (@ 14.7 psia) |
|---|---|---|
| 62.7 | | 70% MeOH + 30% DMC |
| 65.0 | MeOH | |
| 74.0 | | 55% DMC + 45% EtOH |
| 77.5 | | 89% DMC + 11% $H_2O$ |
| 78.2 | | 96% EtOH + 4% $H_2O$ |
| 78.3 | EtOH | |
| 90.0 | DMC | |
| 91.0 | | 70% DEC + 30% $H_2O$ |
| 100.0 | $H_2O$ | |
| 126.0 | DEC | |

The formation of these various azeotropes complicates downstream separation steps such that they cannot be easily or effectively performed by conventional distillation methods.

Several methods have been suggested to overcome these product separation problems.

U.S. Pat. No. 3,963,586 to Ginnasi et al. discloses a process for separating dimethyl carbonate from a mixture of dimethyl carbonate, methyl alcohol, and water. In the disclosed process, water is fed to the top of an extraction distillation column at a water solvent to feed ratio by weight of at least 10:1. A stream of methyl alcohol and water with minor amounts of dimethyl carbonate is withdrawn from the bottom of the column while an overhead stream containing dimethyl carbonate, water, and a minor amount of methyl alcohol is directed overhead. The overhead product stream is generally cooled and decanted into a bottom organic phase containing dimethyl carbonate (97%) and water (3%) with a minor amount of methyl alcohol and a top aqueous phase containing a substantial amount of water (87%) with dimethyl carbonate (12%) and methyl alcohol (1%).

Such processes require extensive retrofitting and modifications in order to produce fuel blending components. For example, the organic phase containing 97% dimethyl carbonate and 3% water still generally requires desiccation or reprocessing in a water fractionation step or through other means in order to reduce the water content of the fuel sufficiently for fuels blending. Similarly, the aqueous phase containing 12% dimethyl carbonate must be undesirably reprocessed to the extraction distillation column along with the water component, at the expense of energy and capacity penalties. Moreover, processes that operate at a solvent to feed ratio by weight in excess of 10:1 can require distillation extraction columns having excessively large and thereby costly vessel diameters.

U.S. Pat. No. 4,162,200 to Himmele et al. discloses a process for obtaining dimethyl carbonate from its solutions in methanol by extractive distillation with an aprotic extractant at a column temperature profile ranging from 60° F. at the top of the column to 250° F. at the bottom. The methanol is generally carried upwards to the overhead product stream, leaving a bottoms product containing the dimethyl carbonate and aprotic extractant. The aprotic extractant is further characterized as:

(a) being substantially inert towards dimethyl carbonate, (b) boiling at a temperature above 100° C. at atmospheric pressure, (c) being miscible with dimethyl carbonate in all proportions, (d) having a dielectric constant, $\epsilon$, of from 4 to 90, and (e) having a dipole moment, $\mu$, of from 1.5 to 5 Debye.

The aprotic extractant is also added at the high extractant to dimethyl carbonate weight ratio of 0.5 to 50 kilograms of extractant per kilogram of dimethyl carbonate. The large volumes of aprotic extractants generally must be separated from the products and recovered at substantial expense to the refiner since these extractants can be costly and furthermore, can contaminate the finished product.

Moreover, processes requiring extractive distillation such as those described above, generally require additional processing equipment such as reboilers, overhead condensers, overhead reflux drums, and phase separators in order to be effective. These systems are particularly costly to procure and erect. Extractive distillation towers also require that an appropriate temperature profile be maintained across the column in order to obtain the desired distillation product cutpoints. These distillation temperature profiles generally conflict with maintaining optimum extraction process temperatures, resulting in cost penalties.

Methods for concentrating solutions containing an alcohol and oxygenates such as organic ethers, aldehydes, ketones, and esters using physical separation means are also known in the art.

U.S. Pat. No. 4,798,674 to Pasternak et al. discloses a process for concentrating mixtures containing dimethyl carbonate and methanol using a membrane-based pervaporation step.

"Opportunities For Membranes in the Production of Octane Enhancers," by Shah et al., AICHE Spring 1989 National Meeting, Symposium Series, Vol. 85, No. 272, pgs. 93–97, also discloses a process for separating dimethyl carbonate and methanol azeotropes across a membrane using pervaporation.

However, physical membrane separation systems such as those described above do not effectively manage three component feedstocks such as water, carbonate, and alkanol. Such systems generally require a drying or water separation step prior to membrane separation. Where water separation by distillation is employed prior to a membrane separation step, carbonate and alkanol can be removed from the feedstock as well, thereby undesirably bypassing the physical separation membrane. This strategy also generally requires that the alkanol to carbonate ratio in the feedstock exceed the ratio in their binary alkanol/carbonate azeotrope (i.e., for example, 7:3 for a mixture of methanol and dimethyl carbonate at atmospheric pressure, otherwise the dimethyl carbonate water azeotrope can further complicate the separation strategy). Moreover, membrane systems have not been particularly reliable in industrial environments and have been known to present operability problems.

It has now been found that feedstocks comprising alkyl carbonates, alkanol, and water can be separated using liquid-liquid extraction, into an extract stream comprising a substantial amount of the alkyl carbonate present in the feedstock and a raffinate stream comprising a substantial amount of the alkanol present in the feedstock. The liquid-liquid process is conducted with two extraction solvents comprising one solvent selective for alkyl carbonates relative to alkanol and a second solvent comprising water selective for extracting alkanol relative to alkyl carbonate.

It has also been found that a solvent selective for extracting alkyl carbonate over alkanol having a gravity of greater than 10° API and less than 100° API provides enhanced liquid-liquid extraction performance through improved raffinate/extract disengaging.

It has also been found that a solvent selective for extracting alkyl carbonates having an aromatic hydrocarbon concentration by weight of greater than 1 percent and an olefinic hydrocarbon concentration by weight of below 80 percent, provides improved extraction of alkyl carbonate from a feedstock comprising alkyl carbonate and alkanol.

It is therefore an object of the present invention to provide an extraction process for a feedstock comprising alkyl carbonate, alkanol, and water that recovers a substantial portion of the alkyl carbonate to an extract product stream and a substantial portion of the alkanol product to a raffinate product stream.

it is another object of the present invention to provide a process that does not require costly extraction distillation columns or require distillation column temperature profiles that are inconsistent with optimum extraction temperatures.

It is yet another object of the present invention to provide a process that does not require physical separation means, such as membrane systems, which can be unreliable in an industrial environment.

It is still another object of the present invention to provide a process that does not require the use of large volumes of costly aprotic polar solvents.

Other objects appear herein.

SUMMARY OF THE INVENTION

The above objects can be achieved by providing a process for separating alkyl carbonate from a feedstock comprising at least one alkyl carbonate and at least one alkanol comprising extracting the alkyl carbonate from the feedstock in a liquid-liquid extraction step comprising a first extraction solvent comprising hydrocarbon selective for extracting alkyl carbonates relative to alkanol in an amount sufficient to extract a substantial portion of the alkyl carbonate from the feedstock and a second solvent comprising water in an amount sufficient to extract a substantial portion of the alkanol from the feedstock.

In another embodiment, the above objects can be achieved by providing a process for separating alkyl carbonate from a feedstock comprising at least one alkyl carbonate having an alkyl radical having 9 or less carbon atoms and at least one alkanol having 9 or less carbon atoms comprising extracting the alkyl carbonate from the feedstock in a liquid-liquid extraction step within a single unitary extraction column comprising a first extraction solvent comprising low polarity hydrocarbon selective for extracting alkyl carbonates relative to alkanol in an amount sufficient to extract a substantial portion of the alkyl carbonate from the feedstock and a second solvent comprising water in an amount sufficient to extract a substantial portion of the alkanol from the feedstock.

The process of the present invention provides substantial benefits over any of the processes or combinations of processes taught in the art.

The process of the present invention can provide substantial separation of alkyl carbonates from water and alkanol in a single unitary liquid-liquid extraction column. Similarly, the process of the present invention can also provide substantial separation of mixtures of alkyl carbonates having various and different alkyl radicals from water and mixtures of various and different alkanols. Moreover, the process operates at extraction column temperature profiles that are entirely independent of distillation steps, which permits further optimization of the liquid-liquid extraction step. Similarly, the subject extraction process does not require reboilers, condensers, and other costly and energy intensive equipment that are generally provided along with distillation towers.

The process of the present invention utilizes a readily available hydrocarbon stream as the solvent selective for extracting alkyl carbonate relative to alkanol and water as the solvent selective for extracting alkanol relative to alkyl carbonate. The process does not require costly pure polar aprotic solvents which further mandate costly solvent recovery steps. However, the refiner retains the flexibility to add solvent recovery steps downstream of the extraction step to reduce solvent requirements. Since many conventional refinery hydrocarbon streams can be used as the solvent selective for extracting alkyl carbonate, the refiner can choose not to recover the solvent and operate on a once-through basis.

The process of the present invention operates at substantially lower solvent to feed ratios than processes in the art. For purposes of the present invention, the term solvent to feed ratio shall mean the total volume of solvent added per volume of alkyl carbonate present in the feedstock. Lower solvent to feed ratios translate into reduced processing costs and permit the erection of smaller extraction devices.

BRIEF DESCRIPTION OF THE INVENTION

Figure 1:
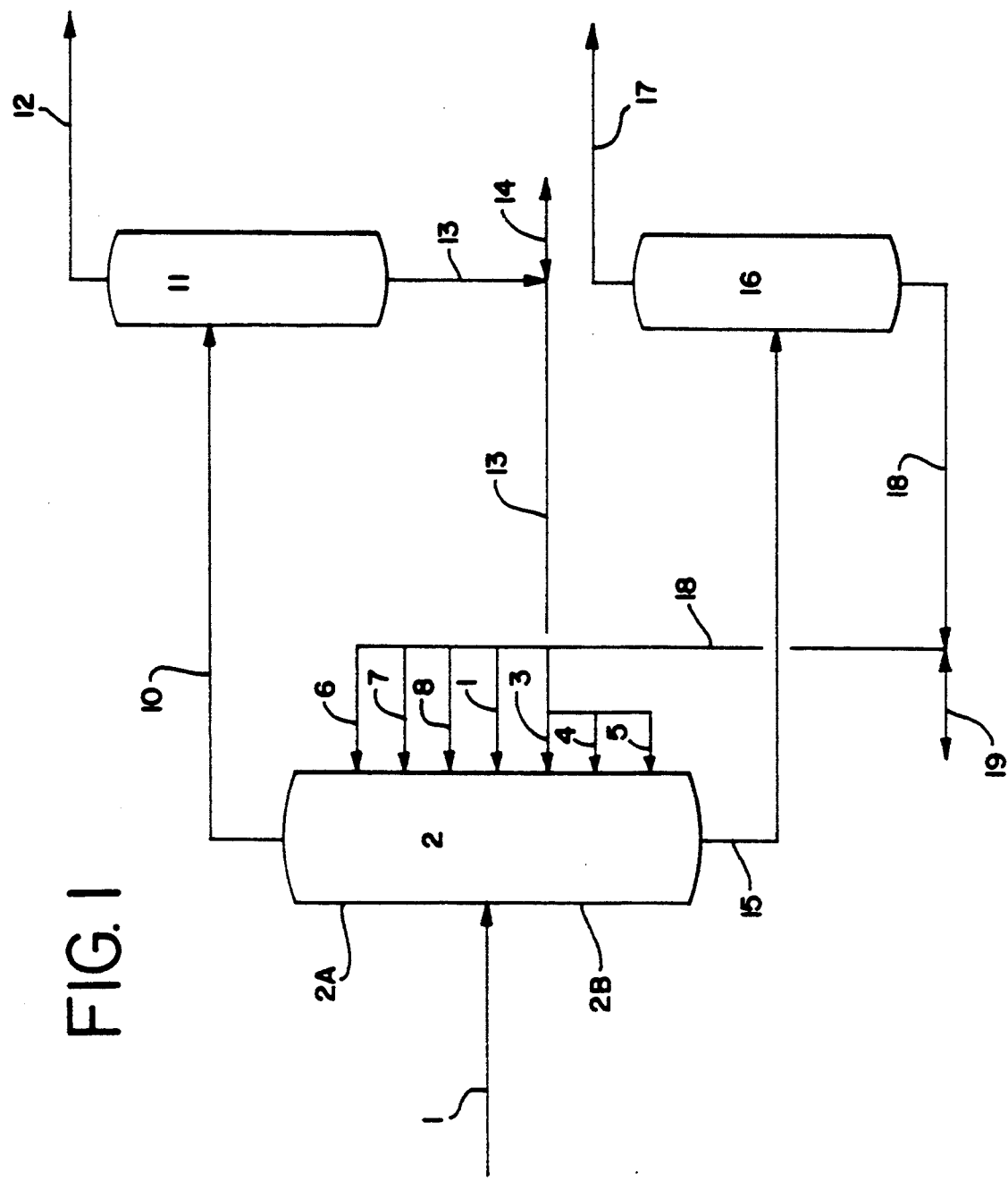
FIG. 1 is a process flow diagram of an alkyl carbonate extraction process in accordance with the process of the present invention.

The feedstock for use with the process of the present invention generally comprises alkyl carbonate, alkanol, and water. The feedstock generally comprises from about 5 percent by weight to about 99 percent by weight alkyl carbonate, preferably from about 10 percent by weight to about 90 percent by weight alkyl carbonate, and more preferably from about 10 percent by weight to about 50 percent by weight alkyl carbonate for best results. The alkanol component is generally present in the feedstock in an amount ranging from about 1 percent by weight to about 99 percent by weight, preferably from about 10 percent by weight to about 95 percent by weight, and more preferably from about 50 percent by weight to about 90 percent by weight for best results. Water is generally present in the feedstock in an amount ranging from about 0.1 percent by weight to about 20 percent by weight, commonly from about 1 percent by weight to about 15 percent by weight, and often from about 2 percent by weight to about 10 percent by weight.

Suitable alkyl carbonate components generally include an alkyl radical having from 1 to 9 carbon atoms, preferably from 1 to 4 carbon atoms, and more preferably from 1 to 3 carbon atoms for best results. The preferred alkyl carbonates are the dialkyl carbonates and in particular, dimethyl carbonate and diethyl carbonate. The alkyl carbonate can also include dialkyl carbonates comprising two different alkyl radicals. Wherein the dialkyl carbonate comprises two different alkyl radicals, the preferred dialkyl carbonate is methyl ethyl carbonate. Similarly, the alkyl carbonate component can comprise a combination of alkyl carbonates.

While any of the above-described alkyl carbonates are suitable for use with the process of the present invention, it is recognized that an end use for the separated alkyl carbonates can be as a gasoline blending component. Where gasoline is the end product to which the alkyl carbonate is blended, it is preferred that the alkyl carbonate substantially boil within the temperature range of from about 50° F. to about 450° F. at atmospheric pressure for best results. Alkyl carbonate components having from 5 to 9 carbon atoms are not generally blended to gasoline since their end point temperature can exceed the end point temperature specification of many gasolines. Where petroleum distillates such as furnace oil and diesel fuel are the end products to which the alkyl carbonate is blended, it is preferable that the alkyl carbonate alkyl radical have from 5 to 9 carbon atoms and that a substantial portion of the alkyl carbonate boil within a temperature span ranging from about 250° F. to about 700° F. at atmospheric pressure for best results.

Another factor to be taken into consideration with regard to alkyl carbonate selection for gasoline use is that while dimethyl carbonate and diethyl carbonate have similar blending octanes in terms of the average of research plus motor octane, diethyl carbonate advantageously has a lower Reid Vapor Pressure (3 psia as compared to 10 psia). This advantage is particularly beneficial to petroleum refiners in view of a recent Environmental Protection Agency decision to reduce the Reid Vapor Pressure requirements for gasolines well below the 10 psia blending Reid Vapor Pressure of dimethyl carbonate.

Moreover, it has now been found that diethyl carbonate can be separated from feedstocks comprising diethyl carbonate, alkanol, and water utilizing the process of the present invention more easily than dimethyl carbonate can be separated from feedstocks comprising dimethyl carbonate, alkanol, and water.

The cost of ethanol relative to methanol may also be factored into a decision of which alkyl carbonate feedstock component to process in accordance with the process of the present invention. External factors such as ethanol subsidies generally can and often do affect the economic balance between methanol and ethanol. Additionally, the demand for methanol and ethanol for ether manufacture may also affect the raw material costs of alkanol feedstocks for the production of alkyl carbonates.

Suitable alkanol components generally include alkanols having from 1 to 9 carbon atoms, preferably from 1 to 4 carbon atoms, and more preferably from 1 to 3 carbon atoms for best results. Generally, the alkanol in the feedstock will correspond to the alkyl radical of the alkyl carbonate. For example, where dimethyl carbonate is the alkyl carbonate, methanol is generally one of the alkanols present in the feedstock. Correspondingly, where diethyl carbonate is the alkyl carbonate, ethanol is generally one of the alkanols present in the feedstock.

The process of the present invention can also accommodate streams comprising a mixture of alkanols. For example, where the alkyl carbonate feedstock comprises mixtures of alkyl carbonates such as dimethyl carbonate, diethyl carbonate, dipropyl carbonate, and diisopropyl carbonate, and asymmetric dialkyl carbonates such as methyl-ethyl carbonate, methyl-isopropyl carbonate, methyl-propyl carbonate, ethyl-isopropyl carbonate, ethyl-propyl carbonate, and propyl isopropyl carbonate, the feedstock can include mixtures of alkanols such as methanol, ethanol, isopropanol, and propanol.

Mixed alkanols can also be directed to the process from external sources. For example, the feedstock can be supplemented with various refinery streams that contain hydrocarbon which can be managed in a manner similar to that described in the present invention. It is anticipated that various refinery and chemical plant streams may contain components that can be separated and recovered utilizing the downstream separation steps described herein. For example, refinery ether production facilities can be integrated with the process of the present invention to consolidate alkanol recovery equipment into a single cost-effective system. In this manner, alkanol mixtures can enter the extraction process from external and supplemental injections. Where the alkanol stream is recovered from the separation process and recycled back to the carbonate formation step, the alkanol from the external and supplemental stream can also reappear in the feedstock comprising the alkyl carbonate.

The water component of the process of the present invention is generally formed as a by-product of many of the alkyl carbonate-forming reactions. Where water is particularly undesirable with prior art processes due to the formation of azeotropes which can complicate separation steps, water does not pose a substantial operating limitation to the process of the present invention. In fact, the process of the present invention is particularly suited to accommodate relatively high water concentrations in the feedstock.

While the process of the present invention is particularly suited to accommodating separation of alkyl carbonate and methanol in the presence of water, the present invention is also suited to processing feedstock streams that are non-aqueous. For purposes of the present invention, the term "non-aqueous" shall mean a feedstock containing less than 0.1 percent by weight water. For purposes of the present invention, the term "non-aqueous" liquid-liquid extraction step shall mean an extraction step in a liquid-liquid extraction column wherein the weight of water is less than 0.5 percent by weight, calculated as a fraction of the total weight of hydrocarbon and water in the liquid-liquid extraction column.

Sources for the alkyl carbonate component of the feedstock processed in accordance with the present invention can and generally include carbonate manufacturing processes, including but not limited to the carbonylation of alcohols, alkylene carbonate alcoholysis, urea alcoholysis, inorganic methods such as alkylation of metal carbonates, phosgene alcoholysis, among other hypothetical methods that may not have been proven effective or performed commercially.

The source of the alkyl carbonate component and the alkanol can be particularly important in optimizing implementation of the process of the present invention. For example, there can be several source locations in an alkyl carbonate manufacturing process that may provide suitable feedstock streams for use in accordance with the present invention. The feedstock may also be a combination of streams from various locations along the carbonate manufacturing facility. It is anticipated that optimization of the process may dictate that a fraction of one or more of several streams from several locations in various carbonate and alkanol source processes may feed the subject inventive process. Similarly, any recovered products such as alkanol or alkyl carbonate can be processed and recycled, in whole or in part, to various locations on the source facility in order to maximize economic gain. All of the fundamental integrations and optimizations described hereabove are envisioned as embodiments of the process of the present invention.

FIG. 1 is a broad process flow diagram of an alkyl carbonate extraction process in accordance with the process of the present invention.

The feedstock, comprising alkyl carbonate, alkanol, and optionally water is conveyed through conduit 1 to a liquid-liquid extraction column 2. The extraction tower generally comprises a top rectification or rectifying section 2A which is the section of the liquid-liquid extraction column located above the feedstock inlet and a bottom stripper or stripping section 2B located below the feedstock inlet and below the rectifying section 2A.

The liquid-liquid extraction tower generally provides a particular number of theoretical stages of extraction separation. For purposes of the present invention, the term "theoretical stage of separation" shall be defined as a separation step wherein the solvent extracted extract stream and raffinate stream from the extraction step exist in perfect equilibrium with each other at a particular set of process conditions and stage compositions and wherein the facilities exist for separating the product streams. The number of theoretical stages of separation may be provided by a substantially larger number of mechanical plates or trays than the projected number of theoretical stages, wherein tray efficiencies are below 100 percent.

A first solvent, comprising hydrocarbon selective for extracting alkyl carbonates relative to alkanol is added to the liquid-liquid extraction column 2 through one or more of conduits 3, 4, and 5. A second solvent comprising water is added to the liquid-liquid extraction column 2 through one or more of conduits 6, 7, 8, and 9. The solvents generally proceed through the column countercurrently with the first solvent passing upwardly to preferentially extract alkyl carbonate from the feedstock while the second solvent comprising water proceeds downwardly to preferentially extract alkanol from the feedstock.

An overhead stream or extract stream is withdrawn from the top of the extraction column through conduit 10. The extract stream generally contains a substantial portion of the alkyl carbonate component from the feedstock and the first solvent selective for extracting alkyl carbonates. The extract stream from conduit 10 is generally directed to a separation vessel 11 or directly to storage wherein the process is once-through solvent extraction. The separation vessel 11 is provided for separating the extract stream into a stream containing a high concentration of the alkyl carbonate component and a stream containing a high concentration of the first extraction solvent. The separation vessel 11 can be, but is not limited to a single stage flash separator, a distillation column, a stripper column, among other separation devices known to those skilled in the art of chemical separation.

The stream containing a high concentration of alkyl carbonate is conveyed through conduit 12 to any of numerous end uses including, but not limited to commercial chemical uses or gasoline or distillate blending component storage. The stream containing a high concentration of the first extraction solvent is generally conveyed through conduit 13 where the stream is recycled back to supply solvent to first solvent conduits 3, 4, and 5. Come and go conduit 14 is provided as a supply line to provide additional first solvent to the extraction column and to remove excessive amounts of first solvent from the system.

A bottoms stream or raffinate stream is withdrawn from the bottom of the extraction column through conduit 15. The raffinate stream generally contains a substantial portion of the alkanol component from the feedstock and the second solvent comprising water. The raffinate stream from conduit 15 is directed to a separation vessel 16 for separating the raffinate stream into a stream containing a high concentration of the alkanol and a stream containing a substantial amount of the water. This separation vessel 16 can also be, but is not limited to a single stage flash separator, a distillation column, a stripper column, among other separation devices known to those skilled in the art of chemical separation.

The stream containing a high concentration of alkanol is conveyed through conduit 17 to any of numerous end uses including recycling the alkanol back to the carbonate manufacturing process, directing the alkanol to an ether manufacturing process, gasoline blending, or to other commercial chemical uses. The stream containing a substantial amount of the water is generally conveyed through conduit 18 where the stream is recycled back to supply solvent to second solvent conduits 6, 7, 8, and 9. Come and go conduit 19 is provided as a supply line to provide additional second solvent to the extraction column and to remove excessive amounts of second solvent from the system. It is useful to recover and recycle the second solvent comprising water in order to minimize water recovery and reclamation costs although some water rejection may be unavoidable wherein the feedstock contains a substantial amount of water.

The first solvent generally comprises a hydrocarbon solvent selective for extracting alkyl carbonate relative to alkanol. First solvents having low polarity generally provide improved selectivity for extracting alkyl carbonate relative to alkanol. Suitable hydrocarbon solvents selective for extracting alkyl carbonate relative to alkanol generally have an API gravity ranging from about 10° API to about 100° API, preferably from about 20° API to about 100° API, and more preferably from about 30° API to about 100° API for best results. Hydrocarbon having a gravity within these ranges generally facilitates better mixing and extraction performance wherein suitable recoveries of alkyl carbonate to extract and alkanol to raffinate can be achieved with fewer theoretical stages of separation. Moreover, the entrainment of first extraction solvent and water in the extract phase, often indicated by a hazy appearing extract product, is substantially reduced wherein the solvent is within the above gravity ranges.

Preferably, the first extraction solvent has an aromatics concentration of more than 1 percent by weight, preferably ranging from about 5 percent by weight to about 50 percent by weight, and more preferably ranging from about 10 percent by weight to about 40 percent by weight for best results. It has been found that the aromatics concentration of the first extraction solvent correlates favorably with the effectiveness of the solvent for extracting alkyl carbonates. However, where aromaticity becomes excessive, the specific gravity can be increased beyond a level where extract/raffinate separability adversely affects solvent extraction performance.

Preferably, the first extraction solvent has an olefin concentration of less than 80 percent by weight, preferably ranging from about 0 percent by weight to 40 percent by weight, and more preferably from about 0 percent by weight to 25 percent by weight for best results. It has also been found that the olefin concentration of the first extraction solvent correlates inversely with the effectiveness of the solvent for extracting alkyl carbonates.

It has also been found that high proportions of branched paraffinic components can also adversely affect solvent extraction performance. Such components are present in highest concentrations in refinery alkylation and isomerate unit products.

Gasoline boiling range components satisfy many of the first solvent criteria described above. Suitable first solvents generally comprise most refinery hydrocarbon streams boiling at a temperature ranging between from about 50° F. to about 450° F. at atmospheric pressure. These streams include, but are not limited to fluid catalytic cracking process naphtha, fluid or delayed coking process naphtha, light virgin naphtha, heavy virgin naphtha, hydrocracker naphtha, hydrotreating process naphthas, alkylate, isomerate, catalytic reformate, and aromatic derivatives of these streams such as benzene, toluene, xylene, and combinations thereof. The catalytic reformate and catalytic cracking process naphthas can often be split into narrower boiling range streams such as light and heavy catalytic naphtha and light and heavy catalytic reformate, which can be specifically customized for use as a solvent in accordance with the present invention. The preferred streams are light virgin naphtha, catalytic cracking naphthas including light and heavy catalytic cracking unit naphtha, catalytic reformate including light and heavy reformate, and the aromatic derivatives of refinery hydrocarbon streams including benzene and toluene.

Distillate boiling range hydrocarbon has not been regulated for oxygenate content at this time. Therefore, the need for an inexpensive oxygenate for distillate fuels such as diesel fuel and furnace oil is not as pressing as for gasoline. However, distillates also satisfy many of the first solvent criteria described above and can be effective first solvents. Suitable distillate-containing first solvents generally comprise refinery hydrocarbon streams boiling at a temperature ranging from about 150° F. to about 700° F. at atmospheric pressure and preferably from about 250° F. to about 700° F. for best results. These streams include, but are not limited to virgin light middle distillate, virgin heavy middle distillate, fluid catalytic cracking process light catalytic cycle oil, coker still distillate, hydrocracker distillate, hydrotreating process distillate, and the hydrotreated embodiments of these streams. The preferred streams are the hydrotreated embodiments of fluid catalytic cracking process light catalytic cycle oil, coker still distillate, and hydrocracker distillate.

It is also anticipated that one or more of the above hydrocarbon streams can be combined for use as a first solvent. In many cases, extraction performance for the various solvent alternatives may be similar. In these cases, logistics such as the volume availability of a stream, location of the nearest connection, and short term economics may be determinative as to what solvent is utilized. Therefore, the process of the present invention offers substantial flexibility as to solvent alternatives. A further advantage of the non-polar first solvent of the present invention is that the solvent need not be recovered from the overhead extract stream and can proceed directly to gasoline or distillate blending along with the recovered alkyl carbonate. It is preferred that gasoline and distillate boiling range solvents not be commingled as this may require one or more additional separation steps.

The first solvent is generally added to the liquid-liquid extraction column at a solvent to feed volume ratio based on the total volume of solvent added (from all locations) per volume of alkyl carbonate present in the feedstock. The solvent to feed ratio is generally adjusted to provide the desired alkyl carbonate extraction performance level desired. The first solvent to feed ratio for the process of the present invention generally ranges from about 50:1 to about 1:1, commonly from about 30:1 to about 3:1, and often from about 20:1 to about 5:1. The first solvent and alkyl carbonate extraction process in accordance with the present invention provides superior selectivity, substantially lower solvent to feed ratios, and flexible solvent recovery capability compared to many of the other solvents generally described in the art.

The first solvent can generally be loaded in a manner so as to produce an extract containing from about 1 percent by weight to about 50 percent by weight of alkyl carbonate in the total overhead extract steam, commonly from about 2 percent by weight to about 40 percent by weight, and often from about 3 percent by weight to about 30 percent by weight. The first solvent loading is, to some extent, a function of the number of theoretical stages of separation in the extraction column and the two solvent to feed ratios. Columns with more theoretical stages can achieve greater loadings and hence, can operate at lower solvent to feed ratios. Exceeding the loading ranges described above, however, can result in alkyl carbonate losses to the raffinate stream or alkanol losses to the extract stream. Similarly, the process of the present invention can achieve low alkyl carbonate loss levels to the raffinate stream of less than 15 percent by weight of the raffinate, commonly less than 2 percent by weight of the raffinate, and often less than 0.1 percent by weight of the raffinate.

Overall, the process in accordance with the present invention generally recovers a substantial portion of the alkyl carbonate to the extract stream. For purposes of the present invention, a "substantial portion of alkyl carbonate recovery" shall mean the recovery of at least 50 percent by weight of the alkyl carbonate present in the feedstock to the extract stream. It is not uncommon, however, for alkyl carbonate recoveries to exceed as much as 75 percent by weight and often as much as 90 percent by weight or higher.

The second solvent generally comprises a solvent selective for extracting alkanol relative to alkyl carbonate. The preferred second extraction solvent is water provided in an amount to extract a substantial portion of the alkanol from the feedstock.

While water is the preferred second solvent, it is important to note that waste water minimization is an important objective of modern petroleum refineries. Since it is anticipated that there may be some fraction of water present in the feedstock, the water that is used as the second extraction solvent can be recovered from the feedstock and reused for extraction. It is preferred that the process in accordance with the present invention, under steady state operation, not import or minimize the import of water into the process.

Where water is imported into the process, the stream comprising water may be derived from other processes in order to minimize total refinery waste water. These water-containing streams may also contain hydrocarbon and other components in addition to water. It is recommended that the second solvent comprising water be analyzed to check for impurities that can adversely effect the extraction process or contaminate downstream products.

The second solvent is also generally added to the liquid-liquid extraction column at a solvent to feed volume ratio based on the total volume of solvent added (from all locations) per volume of alkanol present in the feedstock. The solvent to feed ratio is generally adjusted to provide the desired alkanol extraction performance level desired. The second solvent to feed ratio for the process of the present invention generally ranges from about 1:0.1 to about 1:10, commonly from about 1:0.3 to about 1:5, and often from about 1:0.5 to about 1:3.

The second solvent can generally be loaded in a manner so as to produce a raffinate containing from about 10 percent by weight to about 90 percent by weight of alkanol in the total bottoms raffinate stream, commonly from about 20 percent by weight to about 80 percent by weight, and often from about 30 percent by weight to about 70 percent by weight. The second solvent loading is also a function of the number of theoretical stages of separation in the extraction column and columns with more theoretical stages can generally achieve greater loadings. Exceeding the loading ranges described above, however, can result in alkanol losses to the extract stream or alkyl carbonate losses to the raffinate stream. Similarly, the process of the present invention can achieve low alkanol loss levels to the extract stream of less than 10 percent by weight of the extract, commonly less than 1 percent by weight of the extract, and often less than 0.1 percent by weight of the extract.

Overall, the process in accordance with the present invention generally recovers a substantial portion of the alkanol to the raffinate stream. For purposes of the present invention, a "substantial portion of alkanol recovery" shall mean the recovery of at least 50 percent by weight of the alkanol present in the feedstock to the raffinate stream. It is not uncommon however, for alkanol recoveries to exceed as much as 80 percent by weight and often as much as 90 percent by weight or higher.

Where the process of the present invention is utilized with multiple alkyl carbonates and/or multiple alkanols, the process can be operated to continue to partition the various alkyl carbonates having various and different alkyl radicals to the extract product stream while partitioning the various and different alkanols to the raffinate product stream. This capability is quite useful and permits the operator to separate such multiple alkyl carbonates and alkanols notwithstanding the fact that the boiling point temperatures at atmospheric pressure of such oxygenates could suggest an inversion of one or more of the multiple components. This aspect of the present invention provides substantial benefits to the refiner faced with the obstacle of recovering alkyl carbonate and/or alkanol from feedstreams having diverse components with wide and diverse boiling point temperatures.

It is important to note, however, that where multiple alkyl carbonates and/or alkanols are processed in a single unitary liquid-liquid extraction tower, additional theoretical stages of separation may be required beyond the number of theoretical stages expected for a single alkyl carbonate from alkanol separation.

Dual solvent liquid-liquid extraction provides numerous favorable synergies to the refiner or chemical plant operator such as substantially lower capital equipment and operating costs, and extraction synergies. The process can also be optimized to the particular needs of the operator based on the particular feedstock, product requirements, and solvents available.

For example, it has been found that the process steps for extracting alkyl carbonate and alkanol from the feedstock can be optimized further by adjusting the solvent injection points in the extraction tower. Each theoretical stage of separation comprises a discrete composition of alkyl carbonate, alkanol, water, and first and second solvents among other components. Depending on these compositions, the various solvent loadings, and the process conditions attendant to these theoretical stages, it has been found that the process can be enhanced by aggressively identifying the best locations to add the various solvents to favorably effect the extraction process. It has also been found that under some conditions, the first and second solvent can function as conflicting cosolvents for the extraction of the alkyl carbonate. This problem can be mitigated by identification of this phenomena, proper design of the liquid-liquid extraction column, and finesse with regard to first and second solvent addition.

The liquid-liquid extraction step in accordance with the process of the present invention can be operated using numerous combinations of hardware and process variables, with various feedstock characteristics, and can be customized to meet wide-ranging product requirements. The overall extraction separation efficiency is generally a function of the number of theoretical stages of separation in the extraction column, whether the theoretical stages are rectifying or stripping, the efficiency of the extraction device and internals, and the feedstock characteristics and product specifications required. For example, more theoretical stages in the rectification section and higher second solvent to alkanol ratios both favorably reduce the level of alkanol that is undesirably withdrawn with the extract. Similarly, more theoretical stages in the stripping section and higher first solvent to alkyl carbonate ratios both favorably reduce the level of alkyl carbonate that is undesirably withdrawn with the raffinate. It has also been found that the particular alkyl radical of the alkyl carbonate can affect the solvent to feed requirements and/or theoretical stages required to extract the alkyl carbonate from the feedstock. For example, diethyl carbonate is generally more easily extracted from a feedstock than dimethyl carbonate and may require fewer theoretical stripping stages or lower first solvent to feed ratios.

The extraction process in accordance with the present invention generally requires at least one theoretical stage of separation, preferably at least two theoretical stages of separation, and more preferably at least three theoretical stages of separation for best results. It is also preferred that the process have at least one stage of rectifying extraction and at least 2 stages and more preferably at least 3 stages of stripping extraction for best results.

The various hardware alternatives for liquid-liquid extraction are generally known to those skilled in the art of chemical separation methods. Suitable liquid-liquid extraction methods include, but are not limited to, single and multiple solvent extraction and rotary extraction.

A commonly used liquid-liquid extraction device is the liquid-liquid extraction column. Liquid-liquid extraction can be conducted with dual solvents in a single mechanism or as single extractions in series. Liquid-liquid extraction is generally conducted counter-currently wherein the liquid having the lower API gravity (i.e., higher density) is added at a location high in the column in a manner so that the liquid will proceed downwardly, and the liquid having the higher API gravity (lower density) is added at a location lower in the column in a manner so that the liquid will proceed upwardly. The lower API gravity liquid may be either the feedstock or the solvent in a single solvent extraction. Wherein dual solvents are employed, the counter-current principles and API gravity considerations still generally apply.

The primary component extracted by the solvent along with the solvent exiting the extraction column is generally referred to as the extract stream. Where dual solvents are employed to extract multiple components and wherein one or more extract streams leave the top of the column and one or more extract streams leave the bottom of the column, the extract stream is generally designated by the operator. For purposes of the present invention wherein dual solvents are employed in the manner described above, the alkyl carbonate and first extraction solvent exiting the top of the liquid-liquid extraction column has been designated as the extract stream.

Liquid-liquid extraction columns can also define two distinct column operating sections known in the art as the rectification section or the rectifying section and the stripper section or stripping section. For purposes of the present invention, the rectification section will be defined as the volume of the liquid-liquid extraction column positioned above the primary feedstock inlet and the stripper section will be defined as the volume of the liquid-liquid extraction column positioned below the primary feedstock inlet.

Liquid-liquid extraction towers also generally comprise mixing and separation internals for increasing separation efficiency. These separation internals generally include mechanisms such as valve, sieve, or bubble cap trays or packing elements including, but not limited to, pall rings, grid packing, or other mechanisms known in the art. The higher the efficiency of these separation internals, the better the extraction performance.

The liquid-liquid extraction device can also include rotary extraction devices wherein the feedstock and solvent(s) are injected into a rotating cylinder comprising a plurality of holes within a cylinder shell. The cylinder is rotated at an angular velocity sufficient for the high density component to migrate outside of the cylinder and into the shell wherein it is removed, and the lower density component to migrate towards the center of the cylinder from where it is withdrawn.

Other separation methods and embodiments are also anticipated for use with the present invention from an understanding of chemical separation methods known in the art.

The liquid-liquid extraction column process conditions can comprise a single extraction temperature ranging from about 32° F. to about 150° F., preferably from about 32° F. to about 120° F., and more preferably from about 32° F. to about 100° F. for best results. Extraction column temperatures below 32° F. can result in the crystallization of the water and alkyl carbonate. Temperatures above these ranges can result in boiling of the alkanol or alkyl carbonate/alkanol azeotrope.

It has been found, however, that the effectiveness of the extraction of alkyl carbonate from the feedstock utilizing the first solvent, can be improved wherein the stripper section reaction temperature is reduced. Where the rectification and stripper temperatures can be controllably maintained at different temperatures, it is preferred that the temperature of the rectification section be maintained at a temperature ranging from about 32° F. to about 200° F., more preferably from about 40° F. to about 160° F., and more preferably from about 50° F. to about 120° F. for best results. It is preferred that the stripper section be maintained at a lower temperature ranging from about 32° F. to about 150° F., preferably from about 32° F. to about 100° F., and more preferably from about 32° F. to about 50° F. for best results.

The lower extraction temperatures can be achieved by refrigerating the first solvent prior to injection into the extraction column stripping section, by providing a refrigerated column pumparound system extending from the stripping section, by designing an internal cooling system within the stripping section of the extraction column such as cooling coils, or by other methods known in the art.

The extraction column pressure generally ranges from about 0 psig to about 100 psig, preferably from about 0 psig to about 75 psig, and more preferably from about 0 psig to about 50 psig for best results. Extraction column pressure has not been shown to substantially effect extraction performance but can impact the maximum allowable extraction temperature.

The extract stream comprising alkyl carbonate and first solvent can be directed to a separation step for concentrating alkyl carbonate and recovering the first extraction solvent for recycling back to the extraction step. An extract stream separation step may not be necessary wherein a suitable and readily available gasoline blending component is utilized as the first solvent. However, separation of the extract stream can advantageously provide a more homogeneous and/or more enriched oxygenate-containing gasoline or distillate blending component which can provide product blending benefits.

The separation step can be a single-stage flash or a multistage fractionation. The overhead product from such a separation will generally contain from about 5 percent by weight to about 100 percent by weight and commonly from about 40 percent by weight to about 80 percent by weight of alkyl carbonate. The balance of the overhead product generally comprises the first solvent and minor amounts of alkanol (less than 5 percent by weight) and water (less than 0.5 percent by weight). Preferably, the overhead stream comprises less than 1 percent by weight alkanol and water combined, and more preferably less than 0.1 percent by weight for best results.

The extract separation step can also be conducted in an existing refinery separation or fractionation system. Full-boiling range gasoline and distillate streams are commonly split or fractionated in modern refineries for various purposes including, but not limited to feedstock preparation for downstream processing units or gasoline blending advantages. It is anticipated that streams such as full-boiling range catalytic cracking unit naphtha, full-boiling range catalytic reformate, and full-boiling range crude unit naphtha can be used as the first extraction solvent in order to take advantage of existing downstream fractionator or splitter facilities. For example, for full-boiling range fluid catalytic cracking unit naphtha, reformate, and crude unit naphtha, the extract separation step in accordance with the present invention can be performed in a fractionator that separates fluid catalytic cracking unit naphtha into light and heavy fractions, reformate into light and heavy fractions, or crude unit naphtha into light and heavy fractions respectively.

Similarly, the separation step can be performed in a multiple-product fractionation system such as a crude unit atmospheric tower, a fluid catalytic cracking unit main fractionator, or other multiple-product systems that may also be present in a refinery. Multiple-product systems provide additional flexibility in that any one or more of several solvent streams may be proximately located and suitable for recycling back to the extraction process.

The bottoms product from such a separation generally comprises the first solvent and minor amounts of alkyl carbonate, alkanol, and water. This fraction can be recycled back to the extraction step to reduce the amounts of make-up first solvent and second solvent comprising water that must be added to the extraction column to maintain performance. The recycle fraction can be directed to the first solvent inlet line or can be directed independently to the extraction column in a more optimal location based on the composition of the stream. For example, it may be preferred that fresh make-up first solvent be added to the bottom of the extraction column and recycled first solvent be added at higher locations in the extraction column if the fresh first solvent contains less alkyl carbonate than the recycled first solvent.

The raffinate stream comprising alkanol and water can also be directed to a separation step for concentrating alkanol and recovering the second extraction solvent comprising water for recycling back to the extraction step. The concentrated alkanol can be directed to any one or more of several locations including but not limited to the carbonate manufacturing process, an etherification process (i.e., MTBE, TAME, ETBE, etc.), directly or indirectly to gasoline blending, or to other processes requiring a stream with high alkanol content. The second solvent comprising water is generally recycled back to the extraction step in a manner so as to reduce the net amount of water that must be environmentally reprocessed.

The separation step can be a single-stage flash or a multistage fractionation and can also be part of an existing facility for alkanol/water separation such as might be present in an ether manufacturing facility. For ethanol and methanol, the overhead product from such a separation generally contains at least 30 percent by weight alkanol, commonly more than 60 percent by weight alkanol, and often more than 90 percent by weight of alkanol. The balance of the overhead product generally comprises the second solvent comprising water and minor amounts of alkyl carbonate (less than 10 percent by weight) and first solvent (less than 0.5 percent by weight). Preferably, the overhead stream comprises less than 10 percent by weight alkyl carbonate and first solvent combined, and more preferably less than 1 percent by weight for best results.

The bottoms product from such a separation generally comprises the second solvent comprising water and fractions of first solvent. This fraction is generally recycled back to the extraction step to reduce the amounts of make-up first solvent and second solvent comprising water that must be added to the extraction column to maintain performance. The recycle fraction can be directed to the second solvent inlet line or can be directed independently to the extraction column in a more optimal location based on the composition of the stream.

The process of the present invention provides substantial benefits over any of the processes or combinations of processes taught in the art.

The process of the present invention can provide substantial separation of alkyl carbonates from water and alkanol in a single unitary liquid-liquid extraction column. The process of the present invention can result in an extract product leaving a single unitary liquid-liquid extraction column with an alkanol concentration of less than 10 percent by weight of the extract and a raffinate product with an alkyl carbonate concentration of less than 15 percent by weight of the raffinate.

The process of the present invention operates at an extraction column temperature profile that is entirely independent of distillation steps which permits further process optimization of the liquid-liquid extraction step. Independent extraction and distillation permits the refiner to operate the stripper extraction section at lower temperatures to improve extraction performance.

The process of the present invention facilitates addition of first and second solvent recovery steps downstream of the extraction step to reduce solvent requirements. Since it has been found that many conventional refinery hydrocarbon streams can be used as the first solvent for extracting alkyl carbonate, the refiner can choose not to recover the first solvent and operate on a once-through basis. The refiner can also choose to use solvents that permit and enhance the use of existing gasoline or multiple-product fractionation systems for performing downstream separation steps.

The process of the present invention operates as an extraction column and not as a distillation tower or combination extraction distillation tower. Distillation towers generally require reboilers, condensers, and other costly equipment. Moreover, distillation systems are also generally more energy intensive. An independent extraction column also permits separation of a mixture of alkyl carbonates from a mixture of alkanols in a single unitary extraction column.

The process of the present invention utilizes a readily available hydrocarbon stream as the first solvent and water as the second solvent. Under some circumstances, the process can be a net consumer of refinery spent water streams providing additional economies. The process does not require costly pure polar aprotic solvents which further mandate costly solvent The process of the present invention also operates at substantially lower solvent to feed ratios than processes in the art. Lower solvent to feed ratios reduce processing costs and permit the erection of smaller extraction devices.

The present invention is described in further detail in connection with the following examples, it being understood that the same are for purposes of illustration and not limitation.

EXAMPLE 1

An experimental laboratory simulation of a five-stage "stripping only" countercurrent extraction was conducted in accordance with the process of the present invention. The case study was performed at bench scale using separatory funnels. The testing approach is described in *Mass Transfer Operations* by Treybal, pages 518–520, 3rd Edition, 1980.

The method utilizes well-shaken separator funnels which generally approach one hundred percent stage efficiency. Therefore, for purposes of the present invention, the number of stages refers to theoretical stages which approximates the separation which can be obtained from a well-shaken separator funnel. Mechanical stages, such as the number of trays in a trayed extraction column or the height of packing in a packed extraction column can be estimated using established techniques to account for stream compositions, process variables, and mechanical design. The experimental method was not devised to meet targeted product specifications but was focussed on repeatable processing steps.

Approximately 33.1 grams of a feedstock comprising about 20 weight percent of dimethyl carbonate, 20 weight percent of water, and 60 weight percent of methanol was directed to an extraction step using 17.7 grams of methylcyclohexane as the alkyl carbonate extraction solvent. The liquid-liquid extraction column was operated with 5 theoretical stages of stripping extraction which simulates the injection of an alkyl carbonate-containing feedstock into the top of a liquid-liquid extraction column having 5 theoretical stages of stripping extraction below the feedstock inlet. This test was referred to as Case A and the composition and weight of the extract and raffinate streams are provided in Table 2. A tabulation of the stage-by-stage composition profile for Case A is provided in Table 3.

TABLE 2

| | CASE | | | | | | | |
|---|---|---|---|---|---|---|---|---|
| | A | | B | | C | | D | |
| Balances, wt, wt % | Wt. gms | Wt % | Wt. gms | Wt % | Wt. gms | Wt % | Wt. gms | Wt % |
| Feed | | | | | | | | |
| DMC (DEC) | 6.7 | 20.0 | 2.0 | 20.0 | 5.2 | 25.0 | (4.0) | (20.0) |
| Water | 6.7 | 20.0 | 2.0 | 20.0 | 1.1 | 5.0 | 4.0 | 20.0 |
| Methanol | 19.9 | 60.0 | 6.0 | 60.0 | 14.7 | 70.0 | 12.0 | 60.0 |
| MCH (Reformate) | 17.7 | | 30.0 | | (50.0) | | 60.0 | |
| Solvent Water | 0.0 | | 6.0 | | 12.0 | | 12.0 | |
| Total | 51.0 | 100.0 | 46.0 | 100.0 | 83.0 | 100.0 | 92.0 | 100.0 |
| Products | | | | | | | | |
| Extract | | | | | | | | |
| DMC (DEC) | 1.1 | 7.2 | 1.6 | 5.4 | 4.7 | 9.2 | (4.2) | (6.8) |
| Water | 0.0 | 0.0 | 0.1 | 0.3 | 0.0 | 0.0 | 0.0 | 0.0 |
| Methanol | 0.1 | 1.0 | 0.0 | 0.0 | 0.3 | 0.5 | 0.0 | 0.0 |
| MCH (Reformate) | 13.6 | 91.8 | 27.4 | 94.3 | (46.1) | (90.3) | 57.9 | 93.2 |
| Total | 14.8 | 100.0 | 29.1 | 100.0 | 51.1 | 100.0 | 62.1 | 100.0 |
| Raffinate | | | | | | | | |
| DMC (DEC) | 4.4 | 14.7 | 0.2 | 1.7 | 0.1 | 0.3 | (0.2) | (0.1) |
| Water | 6.3 | 21.2 | 7.8 | 57.0 | 12.1 | 42.7 | 14.7 | 51.3 |
| Methanol | 18.2 | 61.3 | 5.6 | 41.1 | 15.0 | 53.1 | 13.9 | 48.6 |
| MCH (Reformate) | 0.8 | 2.8 | 0.0 | 0.2 | (1.1) | (3.9) | 0.0 | 0.0 |
| Total | 29.7 | 100.0 | 13.6 | 100.0 | 28.3 | 100.0 | 28.8 | 100.0 |
| Weight Balance | 87.3 | | 92.8 | | 95.7 | | 98.8 | |
| Wt % DMC (DEC) in Feed Recovered to Extract | 16.4 | | 80.0 | | 90.4 | | 105.0 | |
| Wt % Methanol in Feed Recovered to Raffinate | 91.4 | | 93.3 | | 102.0 | | 115.8 | |

TABLE 3

| | | Theoretical Stages/Type | | | | |
|---|---|---|---|---|---|---|
| Liquid Phase | Component | F Feed (g/cc) | 2 Strip. (g/cc) | 3 Strip. (g/cc) | 4 Strip. (g/cc) | 5 Strip. (g/cc) |
| Extract | DMC | 0.070 | 0.063 | 0.064 | 0.056 | 0.051 |
| Extract | Methanol | 0.043 | 0.009 | 0.013 | 0.008 | 0.012 |

TABLE 3-continued

| | | Theoretical Stages/Type | | | | |
|---|---|---|---|---|---|---|
| Liquid Phase | Component | F Feed (g/cc) | 2 Strip. (g/cc) | 3 Strip. (g/cc) | 4 Strip. (g/cc) | 5 Strip. (g/cc) |
| Raffinate | DMC | 0.190 | 0.179 | 0.180 | 0.173 | 0.160 |
| Raffinate | Methanol | 0.544 | 0.535 | 0.540 | 0.537 | 0.579 |

☐ Denotes Product Streams

In Case A, the weight percent of dimethyl carbonate recovered to the extract was small. Case A illustrates that without a rectification section wherein the feedstock inlet is located high in the simulated extraction process column and wherein water is not added to extract the methanol and direct it downwardly to the raffinate product, the methanol and methylcyclohexane can function as conflicting cosolvents for absorbing dimethyl carbonate wherein the methanol functions to bring the dimethyl carbonate down to raffinate product while the methylcyclohexane functions to bring the dimethyl carbonate up to the extract product. This illustrates that the presence of a rectification zone wherein the concentration of methanol in the upper section of the column is substantially reduced, can result in improved dimethyl carbonate absorption by the methylcyclohexane extraction solvent. It should not be concluded that additional stripping stages are adverse since they provide additional contact time between the dimethyl carbonate and the methylcyclohexane extraction solvent. The benefits of additional stripping stages are further illustrated in the stage-by-stage profile where it is clear that dimethyl carbonate concentrations in the bottom of the simulated column continue to drop with each additional theoretical stage.

EXAMPLE 2

An experimental laboratory simulation of a five-stage "stripping and rectifying" countercurrent extraction was conducted using the methods described above with respect to Example 1.

Approximately 10 grams of a feedstock comprising about 20 weight percent dimethyl carbonate, 20 weight percent water, and 60 weight percent methanol was directed to a countercurrent extraction step using 30 grams of methylcyclohexane as the alkyl carbonate extraction solvent and 6 grams of water as the methanol extraction solvent. The liquid-liquid extraction column was operated with 5 theoretical stages of extraction comprising a feedstock inlet stage, 2 theoretical stages of rectification, and 2 stages of stripping. The test was performed to simulate the injection of an alkyl carbonate-containing feedstock into the center of a liquid-liquid extraction column having 2 theoretical stages of rectification and stripping above and below the feedstock inlet respectively with injection of the alkyl carbonate extraction solvent (methylcyclohexane) below the bottom stage of the 5 extraction stages and injection of the water (methanol extraction solvent) above the top stage of the 5 extraction stages. The test was referred to as Case B and the composition and weight of the extract and raffinate streams are provided in Table 2. A tabulation of the stage-by-stage composition profile for Case B is provided in Table 4.

TABLE 4

| | | Theoretical Stages/Type | | | | |
|---|---|---|---|---|---|---|
| Liquid Phase | Component | 2 Rect. (g/cc) | 1 Rect. (g/cc) | F Feed (g/cc) | 1 Strip. (g/cc) | 2 Strip. (g/cc) |
| Extract | DMC | 0.047 | 0.052 | 0.054 | 0.026 | 0.013 |
| Extract | Methanol | 0.000 | 0.001 | 0.004 | 0.003 | 0.003 |
| Raffinate | DMC | 0.032 | 0.047 | 0.055 | 0.049 | 0.022 |
| Raffinate | Methanol | 0.001 | 0.032 | 0.387 | 0.417 | 0.433 |

☐ Denotes Product Streams

In Case B, the percentage of dimethyl carbonate in the feedstock recovered to extract was substantially improved from Case A due to the presence of 2 theoretical stages of rectification and the use of substantially higher methylcyclohexane solvent to dimethyl carbonate feedstock ratios. Case B had a solvent to dimethyl carbonate feedstock ratio by volume of about 5:1 whereas Case A had a solvent to dimethyl carbonate feedstock ratio of about 2.6:1. Similarly, methanol recovery to raffinate was also improved. This was generally the result of adding a water methanol extraction solvent above the simulated rectification section for absorbing methanol that would otherwise exit with the extract product.

EXAMPLE 3

An experimental laboratory simulation of a six-stage "stripping and rectifying" countercurrent extraction using catalytic reformate as the alkyl carbonate extraction solvent was conducted using the methods described above with respect to Example 1.

Approximately 21 grams of a feedstock comprising about 25 weight percent dimethyl carbonate, 5 weight percent water, and 71 weight percent methanol was directed to a countercurrent extraction step using 50 grams of catalytic reformate as the alkyl carbonate extraction solvent and 12 grams of water as the methanol extraction solvent. The catalytic reformate used as the alkyl carbonate extraction solvent was stabilized catalytic reformate wherein a substantial portion of the pentane and lighter hydrocarbon components were removed from the product. Other than this stabilization step, full range reformate was used as the extraction solvent.

The liquid-liquid extraction column was operated with 6 theoretical stages of extraction comprising a feedstock inlet stage, 1 theoretical stage of rectification, and 4 theoretical stages of stripping. The test was performed to simulate the injection of an alkyl carbonate-containing feedstock into a liquid-liquid extraction column having 1 theoretical stage of rectification above the feedstock inlet and 4 stages of stripping below the feedstock inlet with injection of the reformate (alkyl carbonate extraction solvent) below the bottom stage of the 6 extraction stages and injection of the water (methanol extraction solvent) above the top stage of the 6 extraction stages. The test was referred to as Case C and the composition and weight of the extract and raffinate streams are provided in Table 2. A tabulation of the stage-by-stage composition profile for Case C is provided in Table 5.

the alkyl carbonate instead of dimethyl carbonate, ethanol was the alkanol, and the feedrates were increased.

Approximately 20 grams of a feedstock comprising about 20 weight percent diethyl carbonate, 20 weight percent water, and 60 weight percent ethanol was directed to a countercurrent extraction step using 60 grams of methylcyclohexane as the alkyl carbonate extraction solvent and 12 grams of water as the methanol extraction solvent. This test was referred to as Case D and the composition and weight of the extract and raffinate streams are provided in Table 2. A tabulation of the stage-by-stage composition profile for Case D is provided in Table 6.

TABLE 6

| Liquid Phase | Component | Theoretical Stages/Type | | | | |
|---|---|---|---|---|---|---|
| | | 2 Rect. (g/cc) | 1 Rect. (g/cc) | F Feed (g/cc) | 1 Strip. (g/cc) | 2 Strip. (g/cc) |
| Extract | DEC | 0.063 | 0.062 | 0.054 | 0.013 | 0.000 |
| Extract | Ethanol | 0.000 | 0.000 | 0.015 | 0.005 | 0.007 |
| Raffinate | DEC | 0.004 | 0.002 | 0.025 | 0.004 | 0.000 |
| Raffinate | Ethanol | 0.001 | 0.113 | 0.430 | 0.473 | 0.464 |

☐ Denotes Product Streams

TABLE 5

| Liquid Phase | Component | Theoretical Stages/Type | | | | | |
|---|---|---|---|---|---|---|---|
| | | 1 Rect. (g/cc) | F Feed (g/cc) | 1 Strip. (g/cc) | 2 Strip. (g/cc) | 3 Strip. (g/cc) | 4 Strip. (g/cc) |
| Extract | DMC | 0.071 | 0.081 | 0.033 | 0.014 | 0.006 | 0.003 |
| Extract | Methanol | 0.004 | 0.013 | 0.009 | 0.008 | 0.009 | 0.008 |
| Raffinate | DMC | 0.017 | 0.063 | 0.031 | 0.014 | 0.007 | 0.003 |
| Raffinate | Methanol | 0.022 | 0.412 | 0.478 | 0.450 | 0.461 | 0.445 |

☐ Denotes Product Streams

Case C provided a further improvement in the percentage of dimethyl carbonate in the feedstock recovered to extract, over cases A and B. This was believed to have resulted from the use of catalytic reformate as the solvent for dimethyl carbonate extraction as well as from adding 2 more theoretical stages of stripping extraction. While it appeared that methanol recovery to raffinate was also enhanced from the weight balance in Table 1, the tray-by-tray composition comparison from Table 5 indicates that removal of one of the rectifying theoretical stages may have increased methanol losses to extract. Some of the performance parameters may have also been affected by the change in feedstock composition.

EXAMPLE 4

An experimental laboratory simulation of a five-stage "stripping and rectifying" countercurrent extraction was conducted using the methods described above with respect to Example 2 except that diethyl carbonate was Case D illustrates that extraction separations with diethyl carbonate as the alkyl carbonate may be easier to achieve than dimethyl carbonate. The process of Case D achieved better diethyl carbonate recovery to extract and better ethanol recovery to raffinate than Case B having identical theoretical stages of separation and similar proportions of feedstocks and solvents. It is important to note however, that the test volumes in Case D were generally double that of Case B which may have resulted in less testing error.

EXAMPLE 5

An experimental laboratory simulation of an eight-stage "stripping and rectifying" countercurrent extraction using multiple (two different) alkyl carbonates and multiple (two different) alkanols was conducted to determine whether the various alkyl carbonates and alkanols would partition or continue to proceed to extract and raffinate products as before. The alkyl carbonate extraction solvent was octane and the extraction was conducted using the methods described above with respect to Example 1.

Approximately 20 grams of a feedstock comprising about 17 weight percent dimethyl carbonate, 17 weight percent diethyl carbonate, 6 weight percent water, 30 weight percent methanol, and 30 weight percent ethanol was directed to a countercurrent extraction step using 60 grams of octane as the alkyl carbonate extraction solvent and 8 grams of water as the alkanol extraction solvent.

The liquid-liquid extraction column was operated with 8 theoretical stages of extraction comprising a feedstock inlet stage, 2 theoretical stages of rectification, and 5 theoretical stages of stripping. The test was performed to simulate the injection of an alkyl carbonate-containing feedstock into a liquid-liquid extraction column having 2 theoretical stages of rectification above the feedstock inlet and 5 stages of stripping below the feedstock inlet with injection of the octane (alkyl carbonate extraction solvent) below the bottom stage of the 8 extraction stages and injection of the water (alkanol extraction solvent) above the top stage of the 8 extraction stages. The test was referred to as Case E and the composition and weight of the extract and raffinate streams are provided in Table 7. A tabulation of the stage-by-stage composition profile for Case E is provided in Table 8.

TABLE 7

| Balances, Wt, Wt % | CASE E Wt. gms | E Wt % | CASE F Wt. gms | F Wt % |
|---|---|---|---|---|
| Feed | | | | |
| DMC | 3.4 | 17.0 | 4.4 | 17.0 |
| DEC | 3.4 | 17.0 | 4.4 | 17.0 |
| Methanol | 6.0 | 30.0 | 7.8 | 30.0 |
| Ethanol | 6.0 | 30.0 | 7.8 | 30.0 |
| Water | 1.2 | 6.0 | 1.6 | 6.0 |
| Octane | 60.0 | 0.0 | 52.0 | 0.0 |
| Solvent Water | 8.0 | 0.0 | 13.0 | 0.0 |
| TOTAL | 88.0 | 100.0 | 91.0 | 100.0 |
| Products | | | | |
| Extract | | | | |
| DMC | 2.9 | 4.6 | 2.9 | 4.9 |
| DEC | 3.3 | 5.1 | 4.2 | 7.2 |
| Methanol | 0.0 | 0.0 | 0.0 | 0.0 |
| Ethanol | 0.0 | 0.0 | 0.0 | 0.0 |
| Octane | 58.0 | 90.2 | 51.2 | 87.8 |
| Water | 0.1 | 0.1 | 0.1 | 0.1 |
| TOTAL | 64.3 | 100.0 | 58.4 | 100.0 |
| Raffinate | | | | |
| DMC | 0.2 | 1.1 | 0.3 | 1.1 |
| DEC | 0.0 | 0.0 | 0.0 | 0.0 |
| Methanol | 5.5 | 27.1 | 7.7 | 25.9 |
| Ethanol | 5.5 | 27.1 | 7.7 | 25.7 |

TABLE 7-continued

| Balances, Wt, Wt % | CASE E Wt. gms | E Wt % | CASE F Wt. gms | F Wt % |
|---|---|---|---|---|
| Octane | 0.0 | 0.1 | 0.0 | 0.1 |
| Water | 9.0 | 44.6 | 14.1 | 47.2 |
| TOTAL | 20.2 | 100.0 | 29.8 | 100.0 |
| Weight Balance | 96.0 | | 96.9 | |
| Wt % DMC + DEC in Feed recovered to Extract | 91.2 | | 80.1 | |
| Wt % Methanol + Ethanol in Feed Recovered to Raffinate | 91.6 | | 98.7 | |

TABLE 8

| Liquid Phase | Component | 2 Rect. (wt %) | 1 Rect. (wt %) | F Feed (wt %) | 1 Strip. (wt %) | 2 Strip (wt %) | 3 Strip (wt %) | 4 Strip (wt %) | 5 Strip (wt %) |
|---|---|---|---|---|---|---|---|---|---|
| Extract | DMC | 4.6 | 5.0 | 5.0 | 3.5 | 2.6 | 1.8 | 1.1 | 0.5 |
| | DEC | 5.1 | 5.0 | 5.0 | 1.3 | 0.3 | 0.1 | 0.1 | 0.0 |
| | Methanol | 0.0 | 0.2 | 0.3 | 0.2 | 0.2 | 0.2 | 0.2 | 0.2 |
| | Ethanol | 0.0 | 0.1 | 0.7 | 0.5 | 0.4 | 0.4 | 0.4 | 0.3 |
| | Octane | 90.2 | 89.6 | 88.9 | 94.4 | 96.4 | 97.4 | 98.1 | 98.9 |
| | Water | 0.1 | 0.1 | 0.1 | 0.1 | 0.1 | 0.1 | 0.1 | 0.1 |
| Raffinate | DMC | 3.2 | 3.3 | 9.7 | 7.5 | 5.5 | 3.7 | 2.3 | 1.1 |
| | DEC | 0.3 | 0.3 | 2.9 | 0.7 | 0.2 | 0.0 | 0.0 | 0.0 |
| | Methanol | 1.0 | 3.5 | 23.4 | 24.0 | 24.9 | 25.6 | 26.0 | 27.1 |
| | Ethanol | 1.9 | 5.9 | 24.0 | 24.6 | 25.5 | 26.2 | 26.6 | 27.1 |
| | Octane | 0.0 | 0.0 | 0.4 | 0.3 | 0.2 | 0.2 | 0.3 | 0.1 |
| | Water | 93.6 | 87.0 | 39.6 | 42.9 | 43.7 | 44.3 | 44.8 | 44.6 |

☐ Denotes Product Streams

Case E illustrates that multiple alkyl carbonates and multiple alkanols can be effectively separated in accordance with the method of the present invention. In this example, both the dimethyl carbonate and the diethyl carbonate partitioned to extract while both the methanol and ethanol partitioned to raffinate. Case E utilized an additional theoretical stage of rectification and an additional theoretical stage of stripping compared to Example C, yet the total alkyl carbonate recoveries were similar for both cases and the total alkanol recoveries were slightly reduced for Case E. Both Case E and Case C were administered at about a 10:1 solvent to feed ratio. A comparison of Cases E and C illustrate that where multiple alkyl carbonates and alkanols are processed, the theoretical stage requirements and/or solvent to feed ratios may need to be increased to maintain comparable alkyl carbonate and alkanol recoveries.

EXAMPLE 6

An experimental laboratory simulation of an eight-stage "stripping and rectifying" countercurrent extraction using multiple (two different) alkyl carbonates and multiple (two different) alkanols was conducted in a manner similar to that described in Example 5. In Example 6, the alkyl carbonate extraction solvent was reduced slightly while the alkanol extraction solvent was increased. The extraction was conducted using the methods described above with respect to Example 1.

Approximately 26 grams of a feedstock comprising about 17 weight percent dimethyl carbonate, 17 weight percent diethyl carbonate, 6 weight percent water, 30 weight percent methanol, and 30 weight percent ethanol was directed to a countercurrent extraction step using 52 grams of octane as the alkyl carbonate extraction solvent and 13 grams of water as the alkanol extraction solvent. The liquid-liquid extraction column theoretical stages and feed location were identical to that of Example 5. The test was referred to as Case F and the composition and weight of the extract and raffinate streams are provided in Table 7.

without benefit of a reaction or conversion step, light and heavy catalytic naphthas (LCN and HCN) which generally comprise naphthas having from 4 to 7 carbon atoms and from 5 to 12 carbon atoms respectively that have been derived from a fluid catalytic cracking or coking process, and heavy reformate (HUF) which generally comprises a large fraction of aromatics having from about 6 to 12 carbon atoms and that has been derived from a catalytic reforming process. The results of the single-stage extractions are provided in Table 9.

TABLE 9

| Balances, wt % | Alkyl Carbonate Extraction Solvents | | | | |
| --- | --- | --- | --- | --- | --- |
| | LVN | LCN | HCN | HVN | HUF |
| Feed | | | | | |
| DMC | 6.0 | 6.0 | 6.0 | 6.0 | 6.0 |
| Methanol | 18.0 | 18.0 | 18.0 | 18.0 | 18.0 |
| Water | 16.0 | 16.0 | 16.0 | 16.0 | 16.0 |
| Solvent | 60.0 | 60.0 | 60.0 | 60.0 | 60.0 |
| Total, wt % (g) | 100.0 (83.0) | 100.0 (83.0) | 100.0 (83.0) | 100.0 (83.0) | 100.0 (83.0) |
| Products | | | | | |
| Extract | | | | | |
| DMC | 4.8 | 5.4 | 5.6 | 7.0 | 6.9 |
| Methanol | 0.6 | 0.7 | 0.8 | 0.6 | 1.2 |
| Water/Solvent | 94.6 | 93.9 | 93.6 | 92.4 | 91.9 |
| Total, wt % (g) | 100.0 (53.0) | 100.0 (53.6) | 100.0 (52.0) | 100.0 (53.0) | 100.0 (53.6) |
| Raffinate | | | | | |
| DMC | 6.4 | 5.3 | 5.3 | 6.5 | 4.3 |
| Methanol | 48.4 | 48.8 | 48.8 | 48.5 | 49.1 |
| Water/Solvent | 45.2 | 45.9 | 45.9 | 45.0 | 46.6 |
| Total, wt % (g) | 100.0 (28.2) | 100.0 (29.3) | 100.0 (26.2) | 100.0 (30.0) | 100.0 (27.9) |
| Weight Balance | 97.8 | 99.9 | 94.2 | 100.0 | 98.2 |
| Wt % DMC in Feed Recovered to Extract | 51.3 | 57.4 | 58.1 | 73.9 | 73.9 |
| Wt % Methanol in Feed Recovered to Raffinate | 91.0 | 95.2 | 85.4 | 96.9 | 91.5 |
| DMC Distribution Coefficient, wt % E/wt % R | 0.75 | 1.01 | 1.05 | 1.07 | 1.62 |
| Methanol Distribution Coefficient, wt % R/wt % E | 82.7 | 69.5 | 64.3 | 74.5 | 42.5 |
| DMC/Methanol Selectivity | 62.3 | 70.3 | 67.2 | 79.5 | 68.7 |

Case F also illustrates that multiple alkyl carbonates and multiple alkanols can be effectively separated in accordance with the method of the present invention. Reducing the alkyl carbonate solvent to alkyl carbonate in the feed ratio predictably reduced the alkyl carbonate recovery to extract product. Increasing the alkanol solvent to alkanol in the feed ratio predictably increased the alkanol recovery to raffinate product. Examples E and F suggest that an economic balance should be found between theoretical stages of rectification and stripping and the respective extraction solvent to feed ratios for best results.

EXAMPLE 7

Single-stage extractions were conducted using the method described above with respect to Example 1, utilizing various conventional gasoline component streams found in a petroleum refinery as the alkyl carbonate extraction solvent. The feedstock utilized for the tests contained 15 grams of methanol, 5 grams of dimethyl carbonate, 13 grams of water, and 50 grams of the particular test solvent. The solvents tested were light and heavy virgin naphthas (LVN and HVN) which generally comprise hydrocarbon having from between 4 and 7 carbon atoms and from 6 and 12 carbon atoms respectively that have been derived from crude The single-stage extractions indicated that HUF provided the highest dimethyl carbonate Distribution Coefficient, which is calculated as the weight percent of dimethyl carbonate in the extract divided by the weight percent of dimethyl carbonate in the raffinate. The light and heavy catalytic naphthas and heavy virgin naphthas were a distant second with regard to dimethyl carbonate Distribution Coefficient. While not wishing to be bound to any particular theories, this may be attributed in part to the substantially higher aromaticity of the HUF.

The solvent preference order was reversed with respect to the methanol Distribution Coefficient, which is calculated as the weight percent of methanol in the raffinate divided by the weight percent of methanol in the extract. However, all of the methanol Distribution Coefficients were above 40.0.

The dimethyl carbonate to methanol selectivity, which is the product of the dimethyl carbonate and methanol Distribution Coefficients, rates HVN as the best solvent on the basis of selectivity. However, since the fraction of methanol in the extract product and the number of rectification stages were generally small for all of the solvents tested, the dimethyl carbonate Distribution Coefficient may be a more useful criteria for measuring solvent effectiveness. Example 6 generally illustrates that HUF, HCN, and HVN are the preferred alkyl carbonate extraction solvents of the solvents tested.

Other embodiments of the invention will be apparent to those skilled in the art from a consideration of this specification or from practice of the invention disclosed herein. It is intended that this specification be considered as exemplary only with the true scope and spirit of the invention being indicated by the following claims.

That which is claimed is:

1. A process for separating alkyl carbonate from a feedstock comprising at least one alkyl carbonate and at least one alkanol comprising extracting said alkyl carbonate from said feedstock in a liquid-liquid extraction step comprising a first extraction solvent comprising hydrocarbon selective for extracting alkyl carbonates relative to alkanol in an amount sufficient to extract a substantial portion of said alkyl carbonate from said feedstock and a second solvent comprising water in an amount sufficient to extract a substantial portion of said alkanol from said feedstock.

2. The process of claim 1 wherein said alkyl radical of said alkyl carbonate has from 1 to 9 carbon atoms and said alkanol has from 1 to 9 carbon atoms.

3. The process of claim 1 wherein said liquid-liquid extraction is conducted in a single unitary liquid-liquid extraction column.

4. The process of claim 1 wherein said first extraction solvent having a boiling range spanning from about 50° F. to about 450° F. at atmospheric pressure comprises one or more low polarity hydrocarbon streams selected from the group consisting of fluid catalytic cracking unit naphtha, coker naphtha, light virgin naphtha, heavy virgin naphtha, hydrocracker naphtha, resid hydroprocessor naphtha, catalytic reformate, alkylate, and isomerate.

5. The process of claim 3 wherein said single unitary extraction column defines a feedstock inlet, a top rectification section defining an overhead outlet, located above said feed inlet, and a bottom stripping section defining a bottoms outlet, located below said feedstock inlet.

6. The process of claim 5 wherein said first extraction solvent comprising hydrocarbon selective for extracting alkyl carbonates relative to alkanol is added to said bottom stripping section and said second solvent comprising water is added to said top rectification section.

7. The process of claim 5 wherein a large portion of said substantial portion of said alkyl carbonate and said first extraction solvent exits said single unitary extraction column as overhead product through said overhead outlet and a large portion of said substantial portion of said alkanol and said second solvent comprising water exits said single unitary extraction column as bottoms product through said bottoms outlet.

8. The process of claim 5 wherein said first extraction solvent contains at least 5 percent by weight aromatic hydrocarbon, less than 80 percent by weight olefinic hydrocarbon, and has a boiling range spanning from about 50° F. to about 450° F. at atmospheric pressure.

9. The process of claim 7 wherein at least one of said overhead product and said bottoms product are directed to a separation step for separating one or both of said first and second solvents from said products and redirecting one or both of said solvents back to said single unitary liquid-liquid extraction column.

10. The process of claim 7 wherein at least 75 percent by weight of said alkyl carbonate present in said feedstock is recovered to said overhead product and at least 80 percent by weight of said alkanol present in said feedstock is recovered to said bottoms product.

11. A process for separating alkyl carbonate from a feedstock comprising at least one alkyl carbonate having an alkyl radical having 4 or less carbon atoms and at least one alkanol having 4 or less carbon atoms comprising extracting said alkyl carbonate from said feedstock in a liquid-liquid extraction step within a single unitary extraction column comprising a first extraction solvent comprising nonpolar hydrocarbon selective for extracting alkyl carbonates relative to alkanol in an amount sufficient to extract a substantial portion of said alkyl carbonate from said feedstock and a second solvent comprising water in an amount sufficient to extract a substantial portion of said alkanol from said feedstock.

12. The process of claim 11 wherein said first extraction solvent has a boiling range spanning from about 50° F. to about 450° F. at atmospheric pressure and comprises one or more low polarity hydrocarbon streams selected from the group consisting of light virgin naphtha, fluid catalytic cracking unit naphtha, catalytic reformate, benzene, and toluene.

13. The process of claim 11 wherein said single unitary extraction column defines a feedstock inlet, a top rectification section defining an overhead outlet, located above said feed inlet, and a bottom stripping section defining a bottoms outlet, located below said feedstock inlet.

14. The process of claim 13 wherein said first extraction solvent comprising hydrocarbon selective for extracting alkyl carbonates relative to alkanol is added to said bottom stripping section and said second solvent comprising water is added to said top rectification section.

15. The process of claim 13 wherein a large portion of said substantial portion of said alkyl carbonate and said first extraction solvent exits said single unitary extraction column as overhead product through said overhead outlet and a large portion of said substantial portion of said alkanol and said second solvent comprising water exits said single unitary extraction column as bottoms product through said bottoms outlet.

16. The process of claim 13 wherein said first extraction solvent contains at least 10 percent by weight aromatic hydrocarbon, less than 40 percent by weight olefinic hydrocarbon and has a boiling range spanning from about 50° F. to about 450° F. at atmospheric pressure.

17. The process of claim 15 wherein at least one of said overhead product and said bottoms product are directed to a separation step for separating one or both of said first and second solvents from said products and redirecting one or both of said solvents back to said single unitary extraction column.

18. The process of claim 15 wherein at least 90 percent by weight of said alkyl carbonate present in said feedstock is recovered to said overhead product and at least 90 percent by weight of said alkanol present in said feedstock is recovered to said bottoms product.

19. The process of claim 11 wherein said feedstock is the product of the oxidative carbonylation of at least one member selected from the group consisting of alkanol having from 1 to 3 carbon atoms.

20. The process of claim 15 wherein said feedstock is the product of the oxidative carbonylation of at least one alkanol having from 1 to 3 carbon atoms, said bottoms product is directed to a separation step for separating said substantial portion of said alkanol from said second solvent comprising water, and at least a portion of said separated substantial portion of said alkanol is redirected to said oxidative carbonylation.

* * * * *